United States Patent
Perry et al.

(10) Patent No.: US 8,460,230 B2
(45) Date of Patent: Jun. 11, 2013

(54) LACRIMAL DRAINAGE MANOMETER AND METHOD OF USE

(75) Inventors: Julian D. Perry, Pepper Pike, OH (US); Craig D. Lewis, East Lansing, MI (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 13/234,242

(22) Filed: Sep. 16, 2011

(65) Prior Publication Data

US 2012/0143117 A1 Jun. 7, 2012

Related U.S. Application Data

(60) Provisional application No. 61/383,372, filed on Sep. 16, 2010.

(51) Int. Cl.
*A61M 1/00* (2006.01)
(52) U.S. Cl.
USPC ................... 604/8; 604/19; 604/21
(58) Field of Classification Search
CPC ..................................... A61M 1/00
USPC ................... 604/8, 9, 11, 15, 19, 21, 27, 264, 604/294
See application file for complete search history.

(56) References Cited

U.S. PATENT DOCUMENTS

| | | | |
|---|---|---|---|
| 5,795,307 A | 8/1998 | Krueger | |
| 5,855,559 A | 1/1999 | Van Tassel et al. | |
| 6,117,086 A | 9/2000 | Shulze | |
| 6,428,502 B1 * | 8/2002 | Lang | 604/28 |
| 8,002,748 B2 | 8/2011 | Donovan et al. | |
| 8,147,479 B1 * | 4/2012 | Wach et al. | 604/522 |
| 2003/0189492 A1 * | 10/2003 | Harvie | 340/573.1 |
| 2004/0171983 A1 * | 9/2004 | Sparks et al. | 604/65 |
| 2006/0129048 A1 * | 6/2006 | Chen et al. | 600/483 |
| 2007/0060820 A1 | 3/2007 | Lofgren et al. | |
| 2007/0112299 A1 * | 5/2007 | Smit et al. | 604/67 |
| 2008/0082008 A1 * | 4/2008 | Ke | 600/499 |
| 2009/0270759 A1 | 10/2009 | Wilson et al. | |
| 2010/0274180 A1 * | 10/2010 | Donovan et al. | 604/65 |
| 2011/0060229 A1 * | 3/2011 | Hulvershorn et al. | 600/486 |
| 2011/0202012 A1 * | 8/2011 | Bartlett | 604/218 |

OTHER PUBLICATIONS

International Search Report and Written Opinion for PCT/US2011/051872, mailed Apr. 23, 2012, pp. 1-9.

* cited by examiner

*Primary Examiner* — Victoria P Shumate
*Assistant Examiner* — Gerald Landry, II
(74) *Attorney, Agent, or Firm* — Tarolli, Sundheim, Covell & Tummino LLP

(57) ABSTRACT

A lacrimal drainage manometer includes a syringe, a pressure sensor operably coupled to the syringe, a flow sensor operably coupled to the syringe, and a user feedback unit. The syringe includes a syringe body and a piston. The syringe body defines a fluid cavity in fluid communication with a cannula, which is configured for insertion into at least a portion of a lacrimal drainage system. The piston is for dispensing a fluid from the fluid cavity through the cannula. The user feedback unit is in electrical communication with each of the pressure sensor and the flow sensor. The user feedback unit is operably coupled to the syringe and configured to provide user feedback based on data from the pressure sensor and/or the flow sensor.

11 Claims, 10 Drawing Sheets

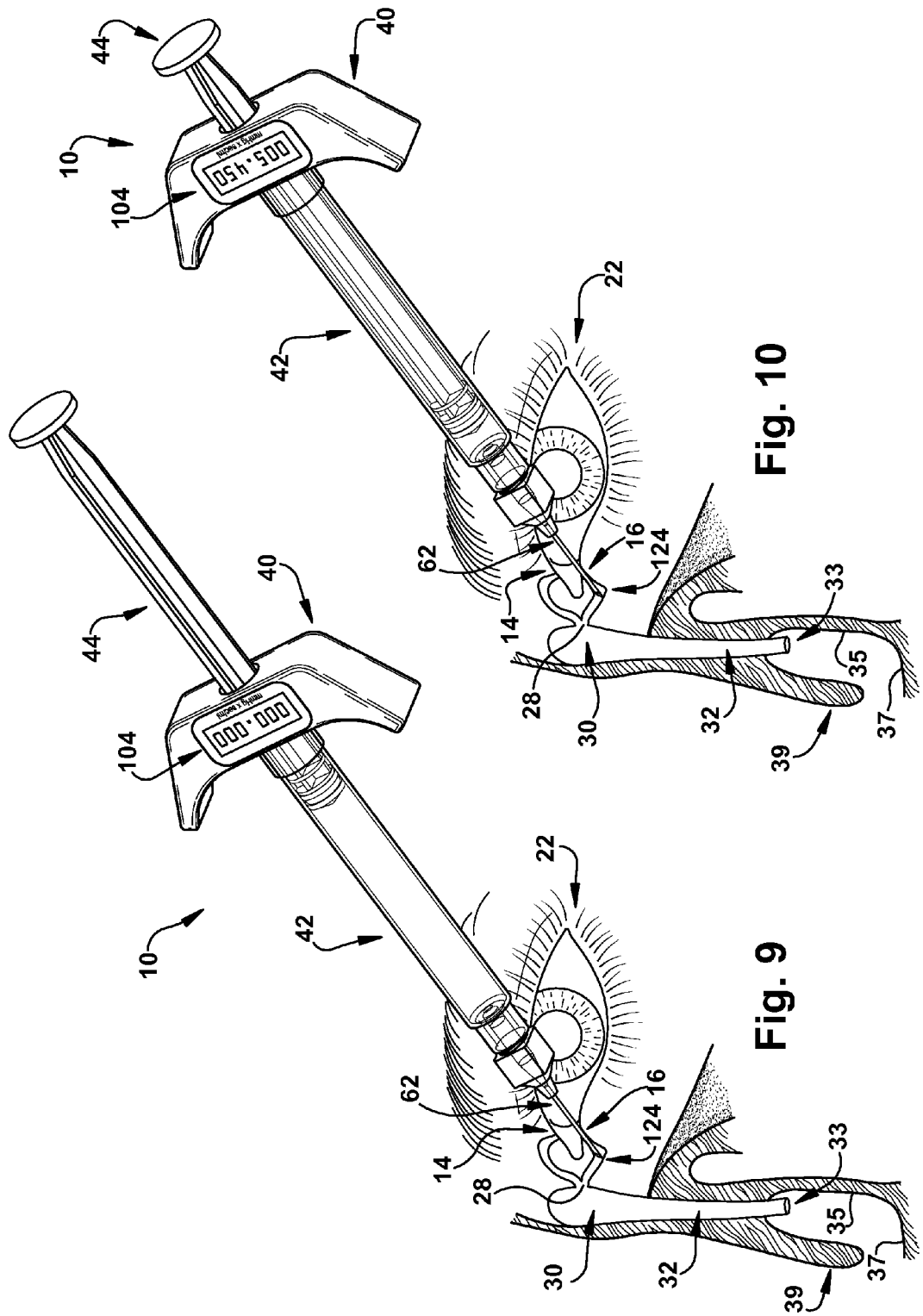

LACRIMAL DRAINAGE MANOMETER AND METHOD OF USE

RELATED APPLICATION

This application claims priority from U.S. Provisional Patent Application Ser. No. 61/383,372, filed Sep. 16, 2010, the subject matter of which is incorporated herein by reference.

TECHNICAL FIELD

The present invention relates generally to devices and methods for assessing the lacrimal drainage system, and more particularly to a lacrimal drainage manometer for determining at least one indicator of lacrimal drainage system function in a subject.

BACKGROUND OF THE INVENTION

Epiphora describes an overflow of tears caused by imperfect drainage of the tear-conducting passages. Epiphora is a common ophthalmic problem, accounting for 3% of ambulatory clinic visits. When tear shedding is extreme, it causes considerable annoyance for patients by degrading visual acuity. The cause of epiphora is usually benign; however, in some cases, malignant nasolacrimal duct obstruction occurs. Current office-based methods for assessing nasolacrimal duct obstruction provide only tactile feedback (i.e., a qualitative measure) for physicians to assess the patency of the nasolacrimal drainage system. Such methods are subjective and prone to overestimation and/or underestimation of lacrimal drainage pressure.

SUMMARY OF THE INVENTION

One aspect of the present invention includes a lacrimal drainage manometer comprising a syringe, a pressure sensor operably coupled to the syringe, a flow sensor operably coupled to the syringe, and a user feedback unit. The syringe includes a syringe body and a piston. The syringe body defines a fluid cavity in fluid communication with a cannula, which is configured for insertion into at least a portion of a lacrimal drainage system. The piston is for dispensing a fluid from the fluid cavity through the cannula. The user feedback unit is in electrical communication with each of the pressure sensor and the flow sensor. The user feedback unit is operably coupled to the syringe and configured to provide user feedback based on data from the pressure sensor and/or the flow sensor.

Another aspect of the present invention includes a method for accurately determining at least one indicator of lacrimal drainage system function during nasolacrimal irrigation. One step of the method includes providing a lacrimal drainage manometer comprising a syringe in fluid communication with a cannula, a pressure sensor operably coupled to the syringe, a flow sensor operably coupled to the syringe, and a user feedback unit in electrical communication with each of the pressure sensor and the flow sensor. Next, a portion of the cannula is inserted into a portion of the lacrimal drainage system. At least one indicator of lacrimal drainage system function is then quantitatively detected during injection of a fluid through the cannula. The at least one indicator of lacrimal drainage system function includes at least one of lacrimal drainage pressure, fluid flow rate, or nasolacrimal resistance.

Another aspect of the present invention includes a method for determining the presence of an obstruction in a lacrimal drainage system. One step of the method includes providing a lacrimal drainage manometer comprising a syringe in fluid communication with a cannula, a pressure sensor operably coupled to the syringe, a flow sensor operably coupled to the syringe, and a user feedback unit in electrical communication with each of the pressure sensor and the flow sensor. Next, a portion of the cannula is inserted into a portion of the lacrimal drainage system. At least one indicator of lacrimal drainage system function is then quantitatively detected during injection of a fluid through the cannula. The at least one indicator is at least one of lacrimal drainage pressure, fluid flow rate or nasolacrimal resistance. An increased or decreased level of the at least one indicator as compared to a control level is indicative of an obstruction.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 9 is a schematic illustration showing the cannula in FIG. 8 advanced into the inferior canaliculus; and FIG. 10 is a schematic illustration showing operation of the lacrimal drainage manometer in FIG. 9.

DETAILED DESCRIPTION

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

In the context of the present invention, it will be understood that when an element, structure, or component is referred to as being "on," "attached" to, "connected" to, "coupled" with, "contacting," etc., another element, structure or component, it can be directly on, attached to, connected to, coupled with or contacting the other element or intervening elements may also be present. In contrast, when an element, structure or component is referred to as being, for example, "directly on," "directly attached" to, "directly connected" to, "directly coupled" with or "directly contacting" another element, there are no intervening elements, structures or components present. It will also be appreciated by those of skill in the art that references to a structure or feature that is disposed "adjacent" another feature may have portions that overlap or underlie the adjacent feature.

As used herein, the term "electrical communication" can include both wired and wireless communication between elements, structures or components of the present invention.

As used herein, the term "subject" can refer to any warm-blooded organism including, but not limited to, human beings, pigs, rats, mice, dogs, goats, sheep, horses, monkeys, apes, rabbits, cattle, etc.

As used herein, the term "lacrimal drainage system" can refer to the structures concerned with tear collection, such as the lacrimal lake, puncta, canaliculi, lacrimal sac, and nasolacrimal duct, as well as the structures described below.

Figure 1A:
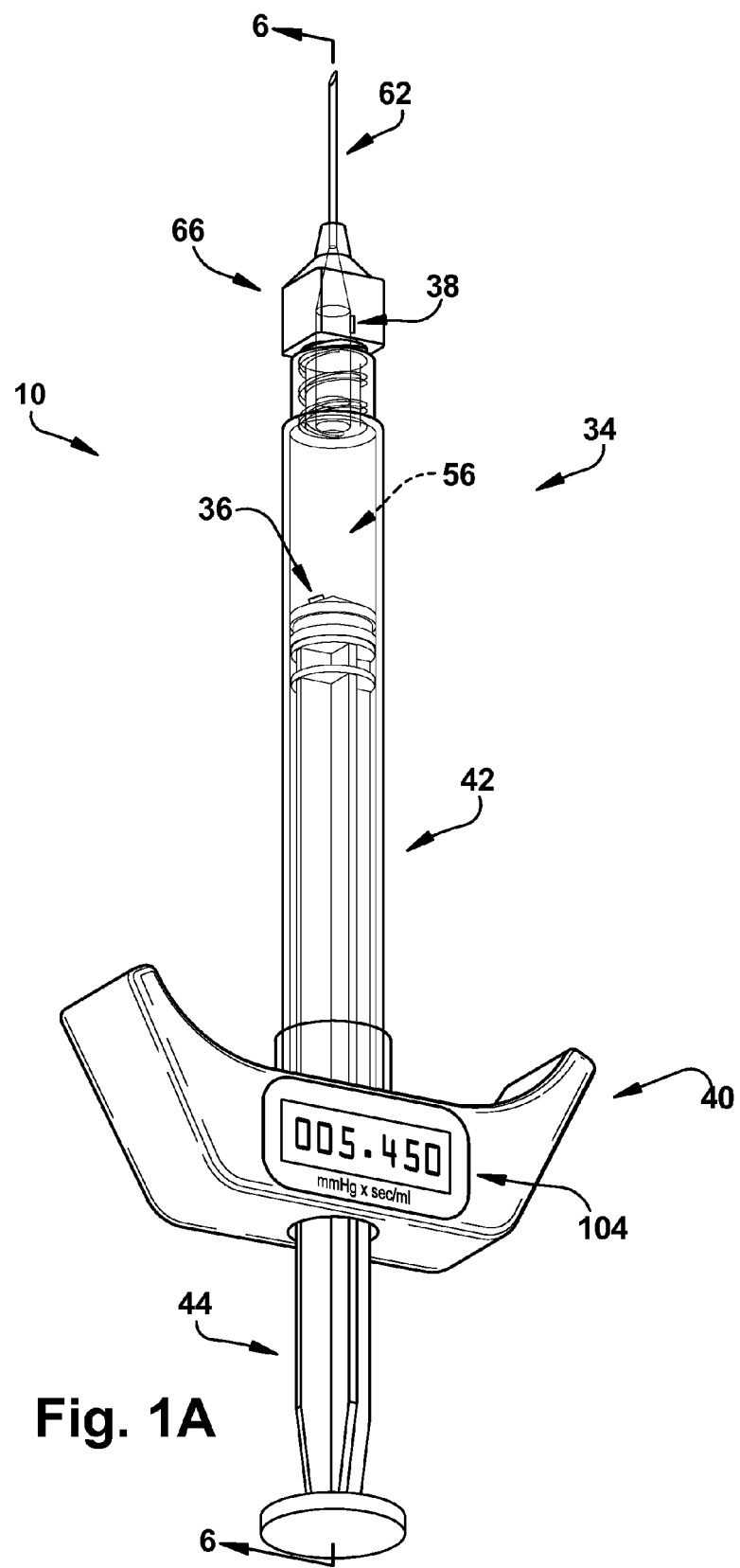
FIG. 1A is an assembled perspective view of a lacrimal drainage manometer comprising a syringe and a user feedback unit constructed in accordance with one aspect of the present invention.
Figure 1B:
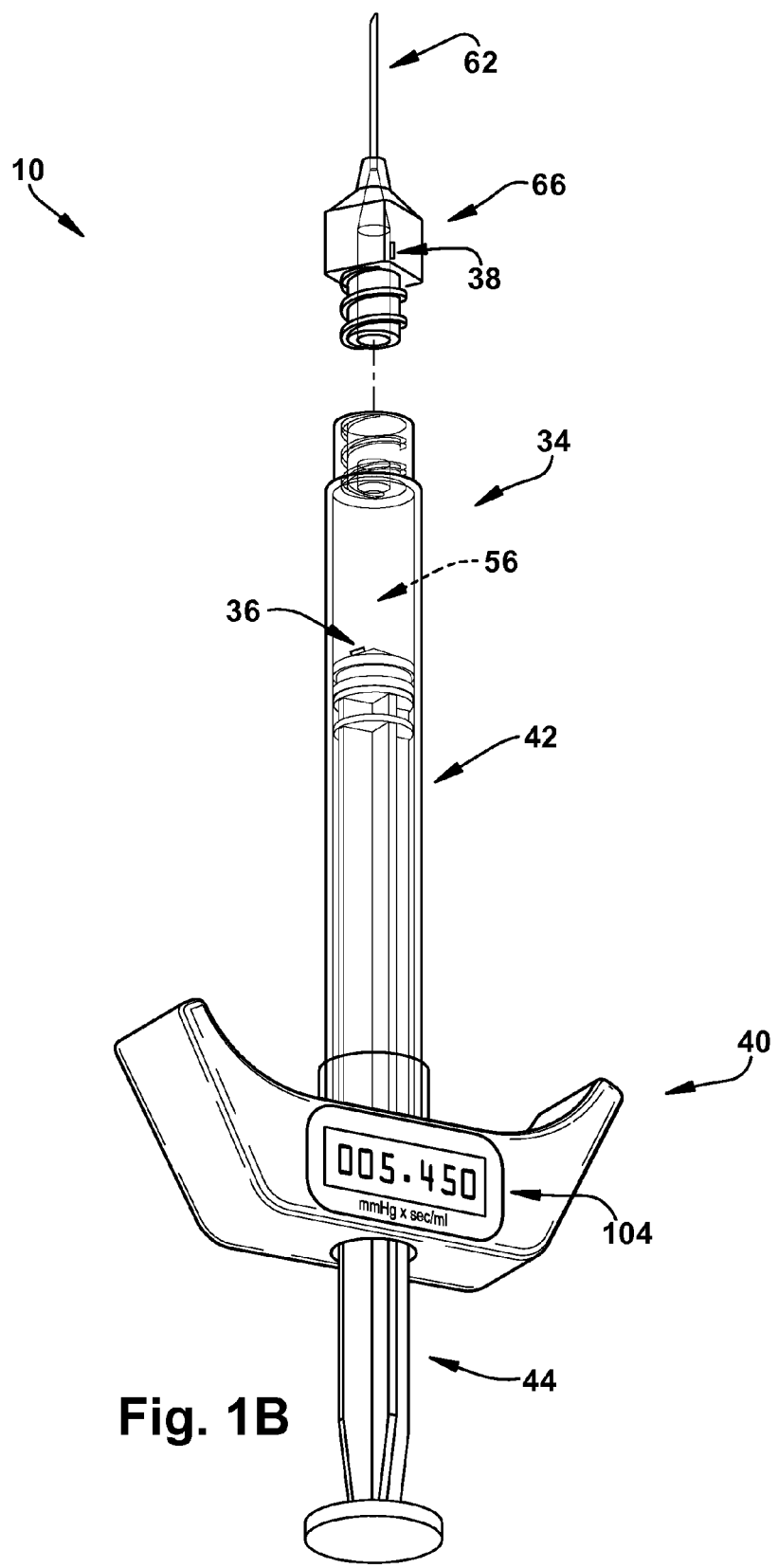
FIG. 1B is an exploded perspective view of the lacrimal drainage manometer in FIG. 1A.
Figure 2:
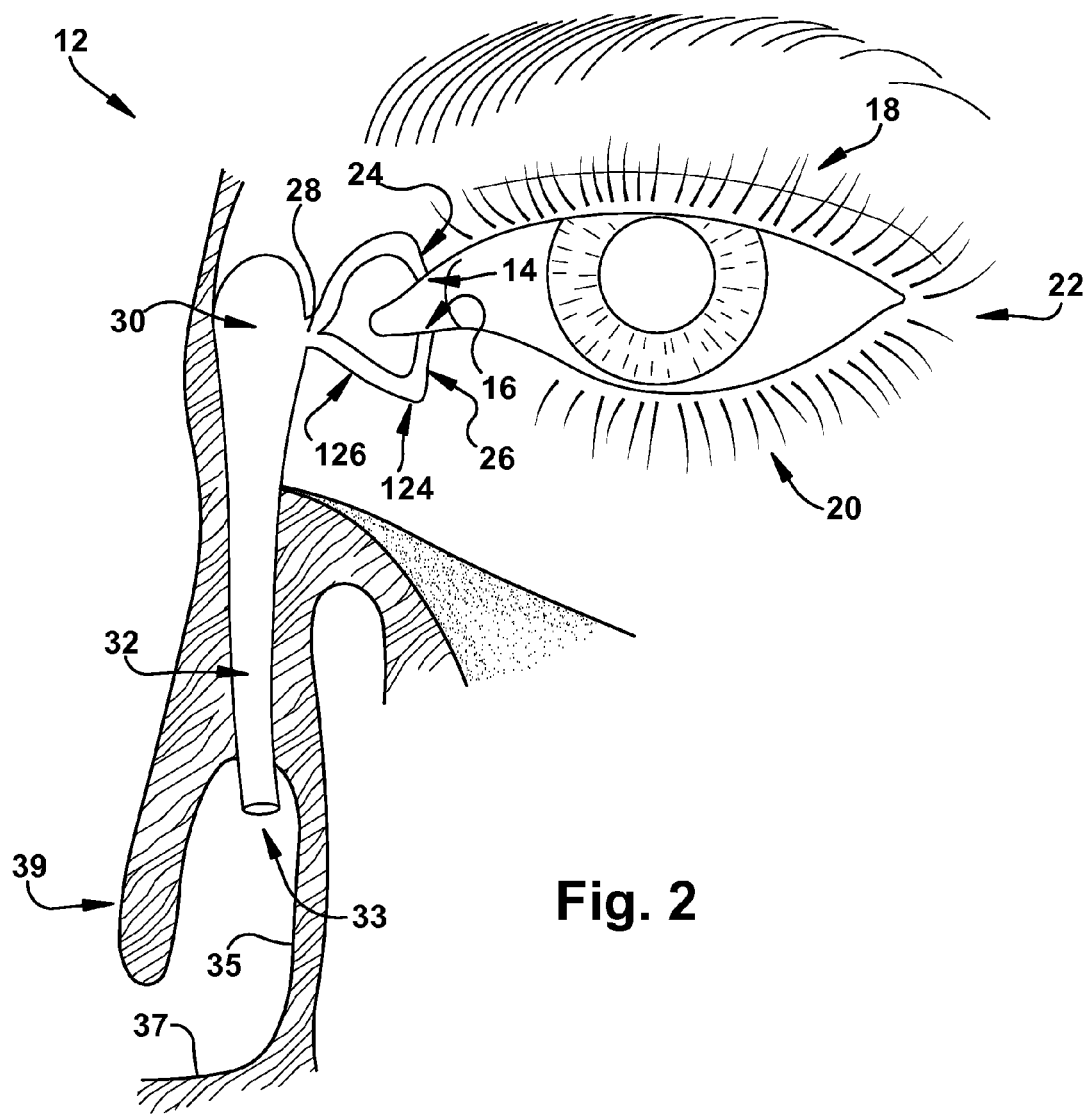
FIG. 2 is a cross-sectional frontal illustration of the lacrimal drainage system of a human subject.

The present invention relates generally to devices and methods for assessing the lacrimal drainage system, and more particularly to a lacrimal drainage manometer for determining at least one indicator of lacrimal drainage system function in a subject. As representative of one aspect of the present invention, FIGS. 1A-B illustrate a handheld lacrimal drainage manometer 10 that may be used, for example, for clinical assessment of suspected nasolacrimal duct obstruction. Unlike conventional approaches to assessing the lacrimal drainage system 12 (FIG. 2), which rely on tactile or qualitative feedback measures, the present invention advantageously provides a lacrimal drainage manometer 10 (FIGS. 1A-B) for quantitatively measuring at least one indicator of lacrimal drainage system function. As described in more detail below, the added quantitative measurements made possible by the present invention provide important clinical information that may be used to help guide the choice of intervention for subjects with a dysfunctional lacrimal drainage system 12 (e.g., epiphora).

A brief description of the relevant anatomy and physiology of the lacrimal drainage system 12 (FIG. 2) is provided to assist the reader with understanding the present invention. The orbital portion of the lacrimal gland (not shown) is located in the superotemporal orbit (not shown), and the palpebral portion of the lacrimal gland is located on the posterior surface (not shown) of the superotemporal upper lid (not shown). The lacrimal gland produces the aqueous portion of the tear film. Ductules (not shown) from the orbital portion of the lacrimal gland pass through the adjacent palpebral lacrimal gland to empty in the superior conjunctival cul-de-sac (not shown). Smaller accessory lacrimal glands in the upper and lower lids also contribute to tear production. The tears bathe the surface of the eye and then drain into the nose via the lacrimal drainage system 12.

The lacrimal drainage system 12 comprises a pair of small openings; namely, the superior punctum 14 and inferior punctum 16, which are located on the medial upper and lower lids 18 and 20 of the eye 22. Tears flow into these puncta 14 and 16, which lead to two small diameter delicate tubes; namely, the superior canaliculus 24 and the inferior canaliculus 26. The canaliculi 24 and 26 join together as a short common canaliculus 28 that enters into the larger lacrimal sac 30. The tears then flow from the lacrimal sac 30 down the nasolacrimal duct 32 and out an opening (not shown), which empties into the nose on the lateral nasal wall (not shown) and onto the nasal floor (not shown) beneath the inferior turbinate (not shown).

Referring to FIGS. 1A-B, the lacrimal drainage manometer 10 comprises a syringe 34, at least one pressure sensor 36 operably coupled to the syringe, at least one flow sensor 38 operably coupled to the syringe, and a user feedback unit 40. The syringe 34 includes a syringe body 42 and a piston 44. The syringe body 42 (FIGS. 3A-B) includes oppositely disposed first and second ends 46 and 48, an outer surface 50, and an inner surface 52. The inner surface 52 and the outer surface 50 define a syringe wall 54. The inner surface 52 of the syringe body 42 defines a fluid cavity 56 that extends between the first and second ends 46 and 48. The first end 46 includes an opening 58 for slidably receiving the piston 44. The second end 48 includes a hollow port 60 for flowing a fluid from the fluid cavity 56 into a cannula 62 (FIGS. 1A-B). The syringe body 42 can be made of any one or combination of known medical grade material(s), such as plastic (e.g., polyethylene).

Figure 3A:
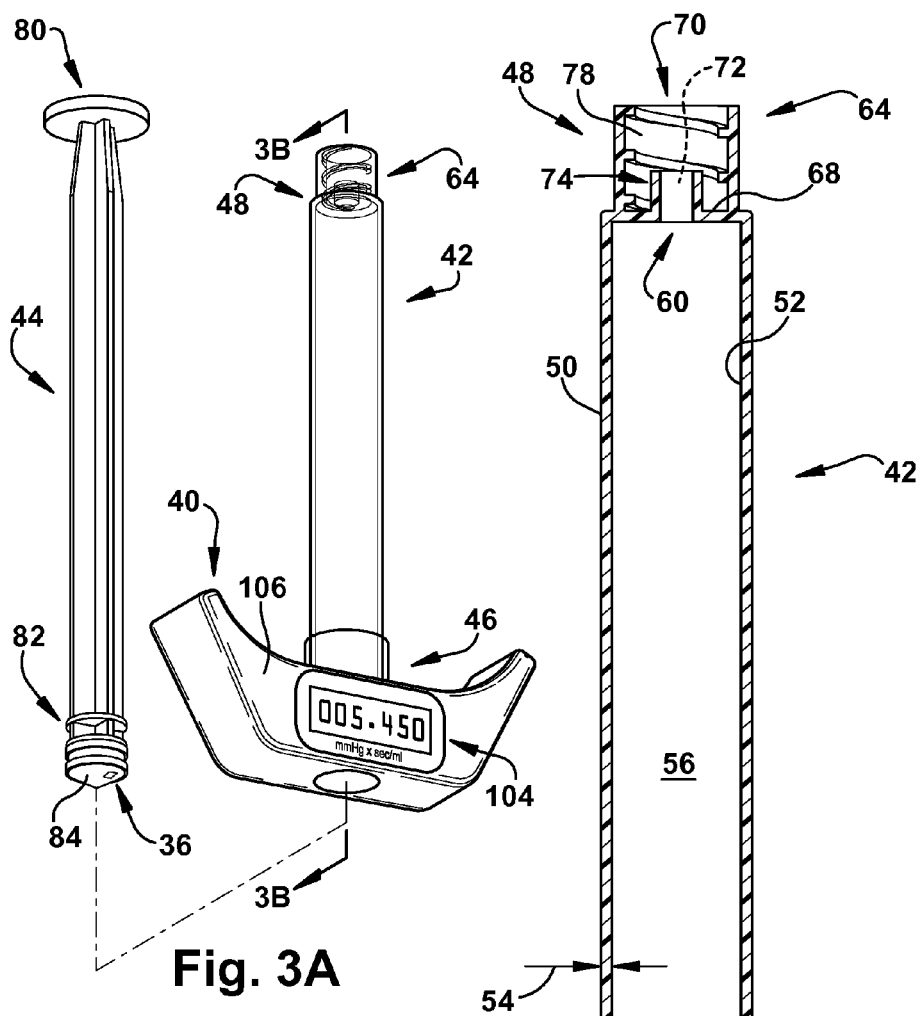
FIG. 3A is a perspective view showing a syringe body of the lacrimal drainage manometer shown in FIGS. 1A-B.
Figure 3B:
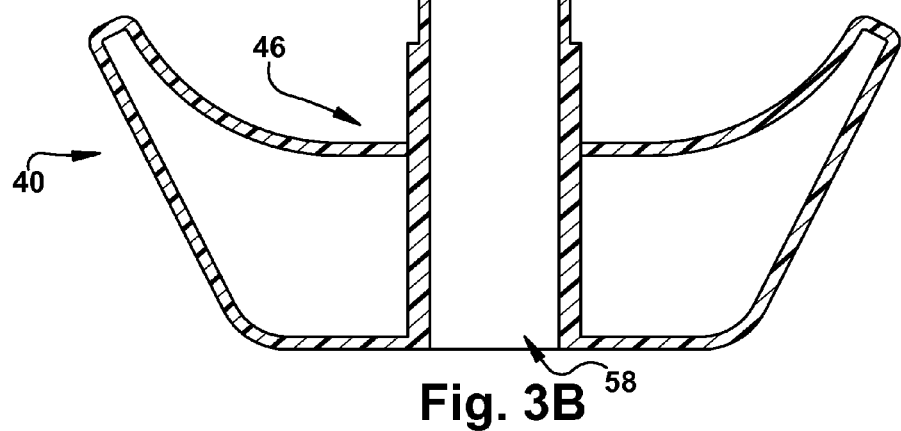
FIG. 3B is a cross-sectional view taken along Line 3B-3B in FIG. 3A.

The second end 48 of the syringe body 42 includes a docking portion 64 configured to releasably mate with a portion of a detachable member 66. As shown in FIGS. 3A-B, the docking portion 64 includes a cavity (not shown in detail) defined by the inner surface 52 of the syringe body 42, an upper surface 68, and a second opening 70, which is configured to receive a portion of the detachable member 66. The hollow port 60 extends from the upper surface 68 into the cavity. The port 60 includes a lumen 72 that is in communication with the fluid cavity 56. A distal end 74 of the port 60 is configured to mate with a lumen 76 (FIG. 5A) of the detachable member 66. The inner surface 52 (FIGS. 3A-B) of the docking portion 64 includes one or more grooves 78 for mating with a portion of the detachable member 66. As shown in FIGS. 3A-B, the groove(s) 64 can be configured in a spiral pattern about the inner surface 52 of the docking portion 64.

The piston 44 (FIG. 3A) is configured to be slidably placed within the fluid cavity 56. The piston 44 has a rod-shaped configuration and includes a handle portion 80 and a distal tip 82. The distal tip 82 includes a distal surface 84 for contacting a fluid and forming a fluid-tight seal with the inner surface 52 of the syringe body 42. The distal tip 82 can be comprised of a flexible or semi-flexible water-proof or water-resistant material, such as rubber. The distal tip 82 is configured so that no pressure can escape from a fluid side of the piston 44 to an atmospheric side of the piston. The piston 44 can be slidably placed in the fluid cavity 56 to cause a fluid (e.g., saline) to be withdrawn or expelled through the cannula 62. All or only a portion of the piston 44 can be can be made of any one or combination of known medical grade material(s), such as plastic.

Figures 4, 5A:
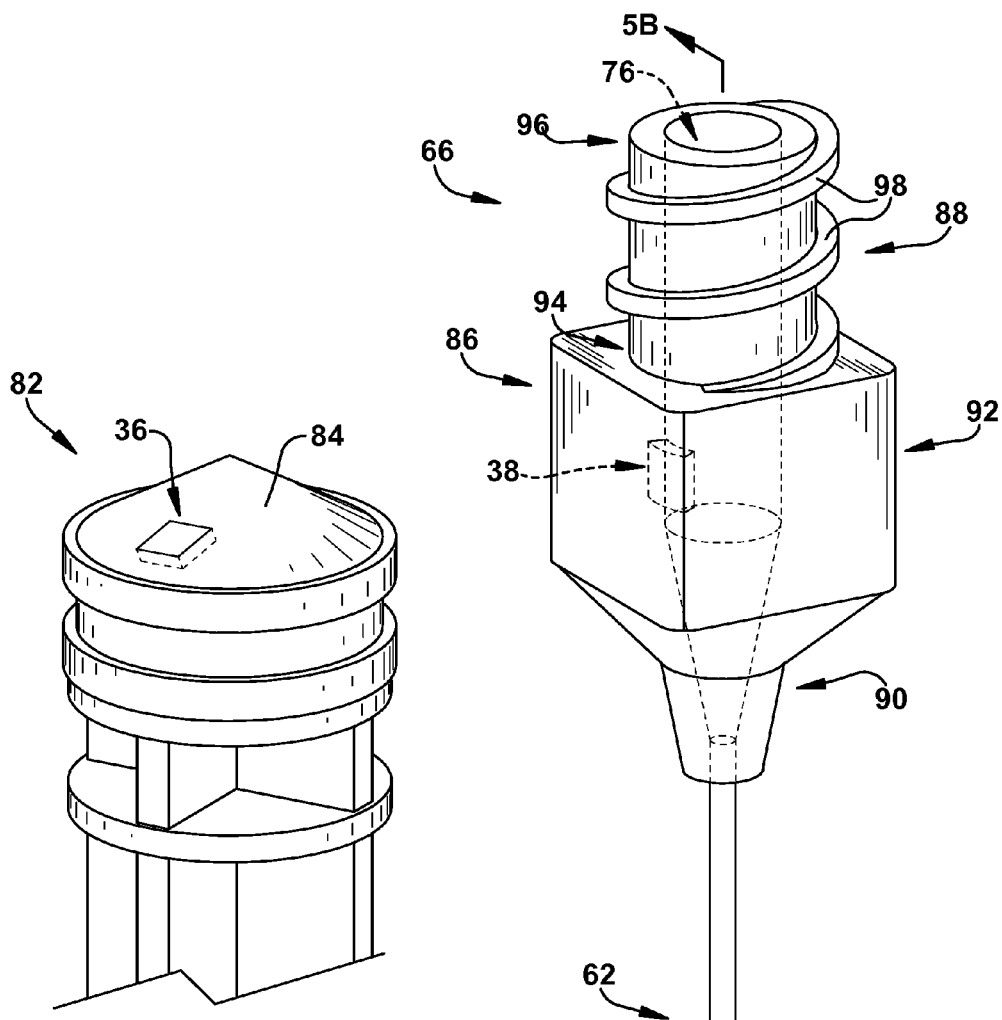
FIG. 4 is a magnified perspective view showing a distal end of a piston comprising the syringe in FIGS. 1A-B.
FIG. 5A is a perspective view showing a detachable member of the syringe in FIGS. 1A-B.

The lacrimal drainage manometer 10 (FIGS. 1A-B) includes a plurality of sensors for determining at least one fluid flow characteristic of a fluid that is injected through the syringe 34 into the lacrimal drainage system 12. As shown in FIGS. 3A, the lacrimal drainage manometer 10 includes at least one pressure sensor 36 that is operably coupled to the syringe 34. For example, a pressure sensor 36 can be attached (e.g., directly attached) to the inner surface 52 of the syringe body 42. Alternatively, a pressure sensor 36 can be integrated into a portion of the wall 54 comprising the syringe body 42. In one example of the present invention, a pressure sensor 36 can operate within a general dynamic pressure range and with a sensing area that is sufficiently small to be mounted to the distal surface 84 of the piston 44 (FIG. 4). Various alternative placements of a pressure sensor 36 (or sensors) will be readily apparent to those skilled in the art.

The pressure sensor 36 measures the pressure being applied to fluid in the fluid cavity 56, and is configured to provide a signal representative of fluid pressure inside the fluid cavity. The pressure sensor 36 is in electrical communication with a circuit (not shown) and/or software (not shown) to provide a user with feedback (e.g., pressure values) via the user feedback unit 40. For instance, the pressure sensor 36 can communicate (e.g., wirelessly) with a digital signal processing circuit (not shown) that is incorporated into the user feedback unit 40. Examples of pressure sensors 36 suitable for use as part of the lacrimal drainage manometer 10 are known in the art and can include, for example, MEMS-based pressure sensors.

Figures 5B, 5C:
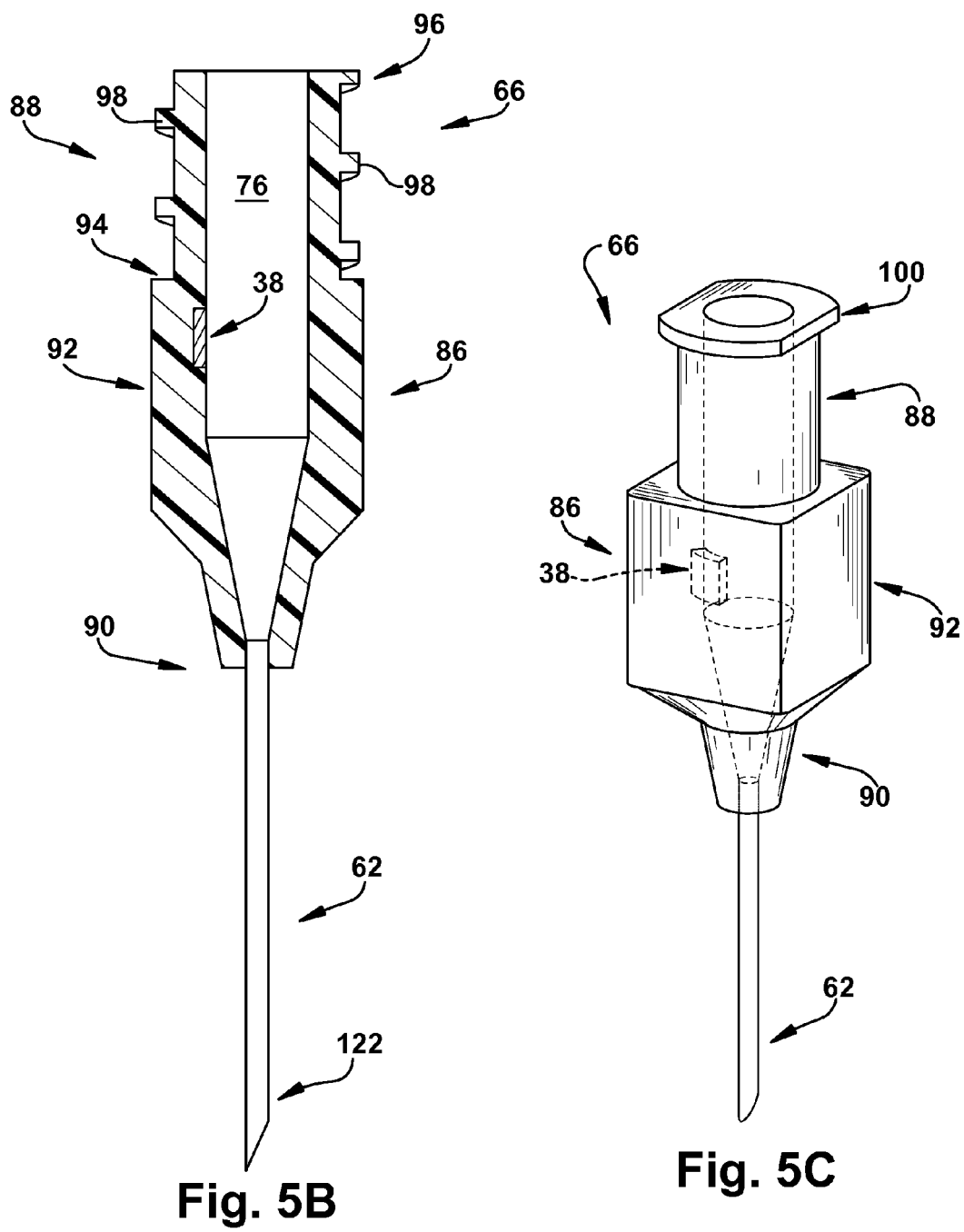
FIG. 5B is a cross-sectional view taken along Line 5B-5B in FIG. 5A.
FIG. 5C is a perspective view showing an alternative configuration of the detachable member in FIG. 5A.

As shown in FIGS. 5A-B, the lacrimal drainage manometer 10 further includes a detachable member 66 configured to releasably mate with the docking portion 64 of the syringe body 42. The detachable member 66 includes a main body portion 86 that is integrally formed with the cannula 62. The main body portion 86 further includes an intermediate portion 92 that extends between first and second ends 88 and 90. The intermediate portion 92 has a cubic configuration to facilitate grasping during attachment of the detachable member 66 to the docking portion 64. It will be appreciated that the intermediate portion 92 can have any other shape or configuration to facilitate ease of attachment to the docking portion 64. For example, the intermediate portion 92 can have a rounded or cylindrical configuration (not shown) and optionally include a tacky surface to facilitate grasping. The detachable member 66 can be made of a medical grade material (e.g., plastic), and can be opaque, semi-opaque, or transparent.

Figure 6:
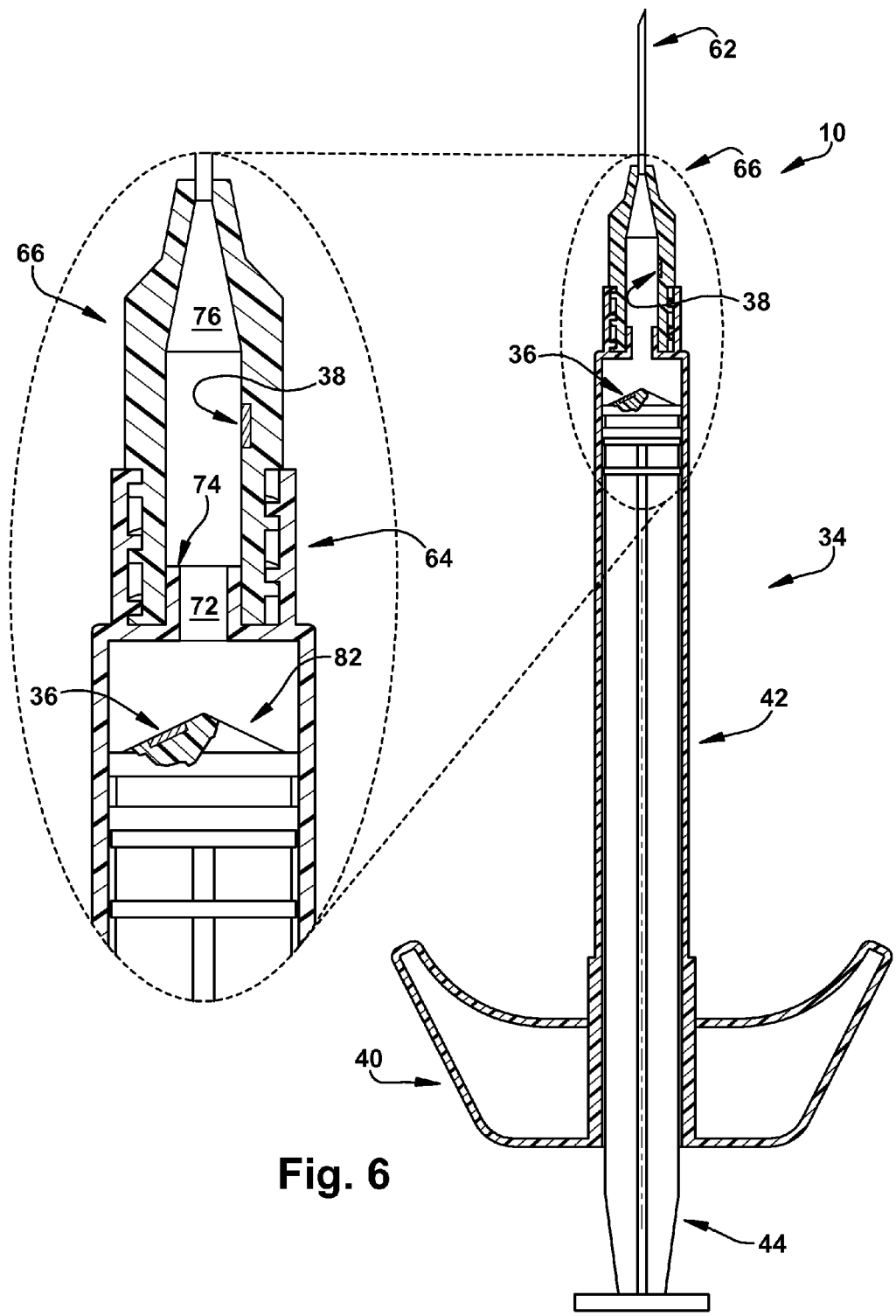
FIG. 6 is a cross-sectional view taken along Line 6-6 in FIG. 1A.

A lumen 76 (FIG. 5B) extends between the first and second ends 88 and 90 of the detachable member 66. The first end 88 is configured to mate with the docking portion 64 of the syringe body 42 such that the lumen 76 and the fluid cavity 56 are in communication with one another (FIG. 6). The first end 88 has a cylindrical configuration and includes oppositely disposed proximal and distal ends 94 and 96. The proximal end 94 is directly attached to the intermediate portion 92. The first end 88 includes a spiral-shaped lip or edge 98 that extends between the proximal and distal ends 96 and 98. The edge 98 is configured to mate with the groove(s) 78 of the docking portion 64 (e.g., by applying torque to the detachable member 66 and/or the syringe body 42). It will be appreciated that the first end 88 of the detachable member 66 and the docking portion 64 of the syringe body 42 can have other configurations, such as a single peripheral edge 100 (FIG. 5C) configured to mate with the groove(s) 78.

The second end 90 of the main body portion 86 has a tapered configuration and is integrally formed with the cannula 62. The tapered configuration of the second end 90 can reduce the profile of the syringe 34 so that the cannula 62 can be more easily visualized during use of the lacrimal drainage manometer 10.

The cannula 62 is configured for insertion into at least a portion of the lacrimal drainage system 12. For example, the cannula 62 can be dimensioned so that a portion of the cannula forms a substantially tight seal when inserted into the lacrimal drainage system 12. The dimensions of the cannula 62 can vary based on the subject's anatomy, the condition being assessed, the procedure being performed, etc. Illustrative cannula sizes can range from 27-gauge to 19-gauge.

The lacrimal drainage manometer 10 includes at least one flow sensor 38 that is operably coupled to the syringe 34. For example, the detachable member 66 can include at least one flow sensor 38 that is operably coupled thereto. As shown in FIGS. 5A-B, a flow sensor 38 can be attached (e.g., directly attached) to the lumen 76 of the detachable member 66. For example, the flow sensor 38 can be integrated into a portion of the wall defining the lumen 76. Alternatively, the flow sensor 38 can be directly attached to the wall that defines the lumen 76. Various alternative placements of the flow sensor 38 (or sensors) will be readily apparent to those skilled in the art.

The flow sensor 38 measures the flow rate of fluid passing through the syringe 34 (e.g., the lumen 76 of the detachable member 66). The flow sensor 38 is configured to provide a signal representative of fluid flow to the user feedback unit 40. The flow sensor 38 is in electrical communication with a circuit (not shown) and/or software (not shown) to provide a user with feedback (e.g., flow value(s)) via the user feedback unit 40. For instance, the flow sensor 38 can communicate (e.g., wirelessly) with a digital signal processing circuit (not shown) that is incorporated into the user feedback unit 40. Examples of flow sensors 38 suitable for use as part of the lacrimal drainage manometer 10 are known in the art and can include, for example, MEMS-based flow sensors.

Referring again to FIGS. 1A-B, the lacrimal drainage manometer 10 additionally comprises a user feedback unit 40 configured to provide user feedback based on data from a pressure sensor 36 and/or a flow sensor 38. The user feedback unit 40 comprises an ergonomically-shaped housing 102. For example, the housing 102 can have a wing-shaped configuration to facilitate ease of handling of the lacrimal drainage manometer 10 (e.g., by a physician). The housing 102 can be releasably, snugly, slidably or frictionally fit about the syringe body 42. For example, the housing 102 can be attached (e.g., directly attached) to the first end 46 of the syringe body 42. The housing 102 can also include a lumen (not shown in detail) configured to allow the piston 44 to be inserted into the fluid cavity 56.

The housing 102 can be compact and cover only a portion of the syringe body 42, thereby allowing a user visual contact with fluid in the fluid cavity 56. The housing 102 can be multi-use while the syringe 34 can be single-use or disposable. The housing 102 can be configured as a lightweight, balanced structure that does not provide eccentric weight or unbalance or unduly affect the injection operation of the lacrimal drainage manometer 10.

The housing 102 includes an integrated display 104 configured to provide an analog, digital, graphical and/or aural indication of sensor data. For example, the display 104 can comprise a screen disposed on, or integrated into, a first side 106 of the housing 102. The display 104 can be configured to provide a user with substantially real-time sensor data (e.g., pressure, flow rate and/or nasolacrimal resistance) during operation of the lacrimal drainage manometer 10. As shown in FIGS. 1A-B, the display 104 can provide a visible readable output of pressure (e.g., 5 mmHg) and flow rate (e.g., 400 sec/ml). It will be appreciated that the display 104 can also include additional features, such as an alarm that audibly or visibly indicates when a safety threshold (e.g., application of excessive pressure during injection) is at risk of being breached during operation of the lacrimal drainage manometer 10.

The user feedback unit 40 can include a power supply (not shown) and/or power saving unit (not shown). The power supply can include a small, high performance battery (not shown) with suitable shape and dimensions for fitting into the housing 102. The power supply and/or power saving unit can include a mechanism for cutting and restoring power in order to save power when the lacrimal drainage manometer 10 is not in use. For example, the power saving unit can cut power when a finger rest (not shown) of the housing 102 has not been pressed for a certain amount of time. The power unit can restore power when the finger rest is pressed.

The user feedback unit 40 is in electrical communication with each of the pressure sensor(s) 36 and the flow sensor(s) 38. For example, the user feedback unit 40 can include a digital processor circuit (not shown) that can be in electrical communication with each of the pressure sensor(s) 36 and the flow sensor(s) 38. The digital processor circuit can be held in the housing 102. The digital processor circuit can communicate (e.g., wirelessly) with the pressure sensor(s) 36 and/or the flow sensor(s) 38 to obtain desired sensor data. The wireless communication between electronic components of the present invention can be carried out, for example, using BLUETOOTH transmission configuration or any other suitable digital communication protocol or configuration.

The user feedback unit 40 can include hardware and/or software configured to:

read a signal from a pressure sensor 36 representative of the fluid pressure in the syringe 34;

convert the signal representative of fluid pressure in the syringe to a pressure value representative of the fluid pressure;

read a signal from a flow sensor 38 representative of the fluid flow rate through the syringe;

convert the signal representative of fluid flow in the syringe to a flow value representative of the fluid flow;

calculate an experienced nasolacrimal resistance to the expelled fluid flow as the quotient between the pressure and the fluid flow; and present the resistance value, the pressure, and/or the flow rate on the display 104.

As noted above, the software and/or hardware of the user feedback unit 40 is configured to calculate a resistance experienced by the syringe 34 when expelling its contents. For example, nasolacrimal resistance can be calculated from flow and pressure data by the aid of the Poiseuille-Hagen equation, or other fluid mechanics equations, which have been incorporated into the software of the user feedback unit 40. The results are visualized on the display 104, and the user can use them to make a decision on further actions.

Figure 7:
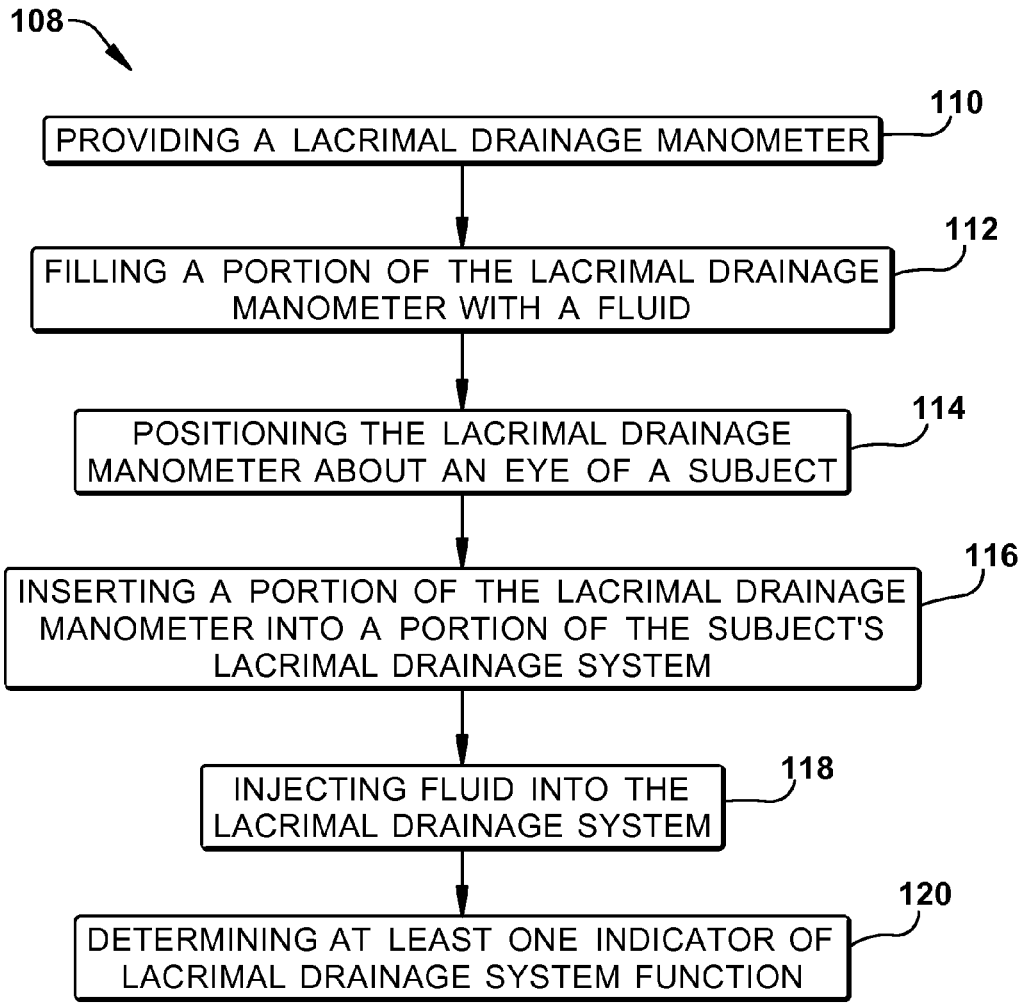
FIG. 7 is a process flow diagram illustrating a method for accurately determining at least one indicator of lacrimal drainage system function during nasolacrimal irrigation according to another aspect of the present invention.

FIG. 7 illustrates another aspect of the present invention comprising a method 108 for accurately determining at least one indicator of lacrimal drainage system function during nasolacrimal irrigation. As described below, the method 108 advantageously provides indicators of lacrimal drainage system function (e.g., pressure readings) during nasolacrimal irrigation, which in turn provide(s) a quantitative measurement for assessing nasolacrimal patency. Determining quantitative measurements of lacrimal drainage system function during nasolacrimal irrigation provides medical practitioners useful information, which can be used to inform subsequent clinical decisions (e.g., quantifying nasolacrimal duct obstruction, guiding the choice of surgical procedure, and determining the success of lacrimal drainage procedure) and/or as an adjunct to tearing evaluation (e.g., in subjects with epiphora).

One step of the method 108 includes providing a lacrimal drainage manometer 10 (Step 110). The lacrimal drainage manometer 10 can be identically or similarly constructed as the lacrimal drainage manometer shown in FIGS. 1A-B and described above. For example, the lacrimal drainage manometer 10 can comprise a syringe 34, at least one pressure sensor 36 operably coupled to the syringe, at least one flow sensor 38 operably coupled to the syringe, and a user feedback unit 40 that is in electrical communication with each of the pressure sensor(s) and the flow sensor(s). As described above, the user feedback unit 40 includes an integrated display 104 configured to provide measured pressure, flow rate, and/or nasolacrimal resistance values during use of the lacrimal drainage manometer 10.

If it has not been done so already, the fluid cavity 56 of the syringe 34 can be filled with a desired volume of a fluid (e.g., sterile saline) at Step 112. To do so, a user can first use tactile force to completely depress the piston 44 within the fluid cavity 56. A distal tip 122 of the cannula 62 can then be immersed in a volume of the fluid. Next, the piston 44 can be withdrawn (i.e., towards the user) to cause the fluid to flow into the fluid cavity 56. The piston 44 can be continuously withdrawn until a desired volume of the fluid fills the fluid cavity 56.

After filling the fluid cavity 56 with a desired volume of fluid, the lacrimal drainage manometer 10 is positioned about the eye 22 (e.g., the inner eye) of the subject (Step 114). For example, the cannula 62 can be positioned adjacent the inferior punctum 16. It will be appreciated that the intended insertion route (e.g., inferior punctum 16 or superior punctum 14) of the cannula 62 into the lacrimal drainage system 12 will depend upon the discretion of the user.

Figure 8:
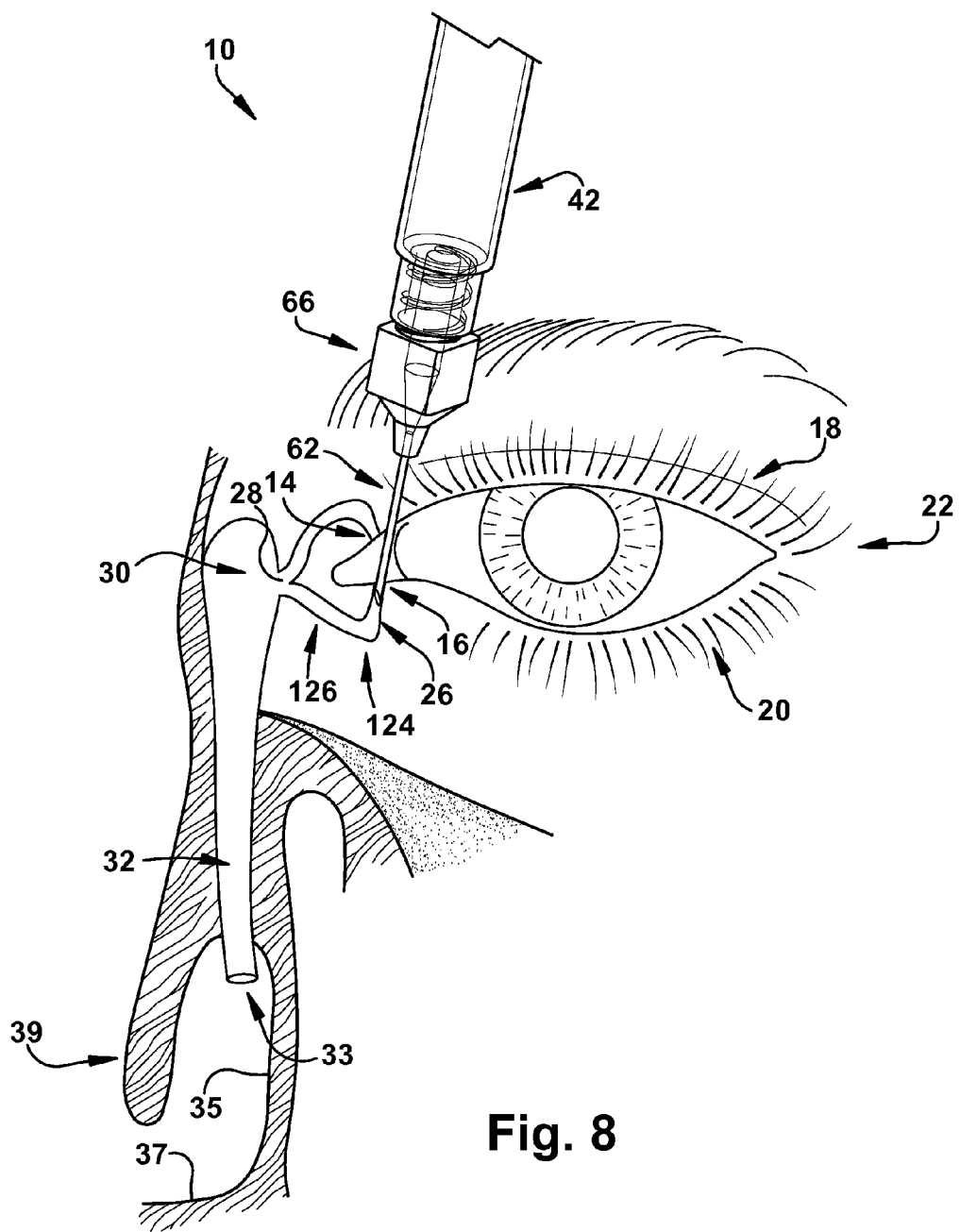
FIG. 8 is a schematic illustration showing a cannula of the lacrimal drainage manometer in FIGS. 1A-B inserted into an inferior punctum of the subject.

At Step 116, a portion of the cannula 62 is inserted into the lacrimal drainage system 12. As shown in FIG. 8, for example, the distal tip 122 of the cannula 62 is inserted into the inferior punctum 16. If needed, one or both of the puncta 14 and 16 can be dilated with a dilator (not shown) prior to insertion of the cannula 62. The distal tip 122 of the cannula 62 can remain essentially where it is inserted or, alternatively, be progressively advanced through the inferior punctum 16 to a desired location. For example, the distal tip 122 of the cannula 62 can be advanced to the inferior ampulla 124 (FIG. 9). Alternatively, the distal tip 122 can be further advanced past the inferior ampulla 124 into a portion of the inferior horizontal canaliculus 126. It will be appreciated that the distal tip 122 of the cannula 62 can be advanced to other locations within the lacrimal drainage system 12, such as the valve of Rosenmüller (not shown) or the lacrimal sac 30.

Once the distal tip 122 of the cannula 62 is appropriately positioned within the lacrimal drainage system 12, the user can apply tactile force to the handle portion 80 of the piston 44 (Step 118). As force is applied to the piston 44, fluid is flowed from the fluid cavity 56, through the lumen 76 of the detachable member 66, and out of the cannula 62 into the lacrimal drainage system 12. During application of force to the piston 44, the pressure sensor 36 provides a signal representative of fluid pressure inside the fluid cavity 56 to the user feedback unit 40 (Step 120). As shown in FIG. 10, for example, the pressure signal can be provided to the digital processor circuit, which then visually displays the pressure (e.g., in mmHg) on the display 104. As described above, the flow sensor 38 may also provide a signal representative of fluid flow (e.g., in sec/ml) through the syringe 34 to the user feedback unit 40. Based on the visualized sensor data, the user can inform his or her decision as to the appropriate course of action. As explained below, for example, the method 108 can be used to determine the presence of an obstruction in the lacrimal drainage system 12.

To determine the presence of an obstruction in the lacrimal drainage system 12, Steps 110-120 can be performed as described above. At Step 120, the determination of at least one indicator of lacrimal drainage system function may also be performed while assessing the lacrimal drainage system 12 using tactile sensation. As described above, the detected pressure, fluid flow rate, and/or nasolacrimal resistance can be visually displayed on the display 104 of the user feedback unit 40.

After determining the level of the at least one indicator of lacrimal drainage system function, the determined level can be compared to a normal or control level. One skilled in the art will appreciate how to determine a normal or control level. For example, the normal or control level may be determined by having previously determined a healthy baseline value of the at least one indicator for a given subject, by averaging normal or baseline levels from a number of healthy subjects, or by referring to a known or validated source of normal or control values (e.g., a medical journal or database).

An increased or decreased level of the at least one indicator (as compared to the control level) can indicate that there is an obstruction in the lacrimal drainage system 12. For example, an increased nasolacrimal resistance and/or pressure level can indicate the presence of an obstruction. Alternatively, a decreased fluid flow rate can indicate the presence of an obstruction. It will be appreciated that an obstruction can be functional or physical. A physical obstruction, for example, can include stenosis, a foreign body, or some other blockage in the lacrimal drainage system 12. Sometimes, the lacrimal drainage system 12 may appear patent by determining normal pressure, flow rate and/or resistance values; however, there may be a functional obstruction, such as collapse of all or part of the lacrimal pathway (e.g., the lacrimal sac 30). Thus, the present invention may be used to determine the nature and position of an obstruction within the lacrimal drainage system 12.

The following example is for the purpose of illustration only and is not intended to limit the scope of the claims, which are appended hereto.

EXAMPLE

Methods

We performed a prospective review of case series. Data was collected on age of patient, gender, duration of symptoms, previous treatments, dye disappearance testing results, percentage of irrigation through the nasolacrimal duct, eyelid laxity, presence of ectropion, and the various pressure measurements.

We quantitatively measured the pressure generated during manual, conventional probing and irrigation using a standard 3 cc syringe, and experimental probing and irrigation using an infusion pump (Medfusion 2010 Infusion Pump, MEDEX Inc., Carlsbad, Calif.) to deliver a constant flow rate of saline. We measured the steady state irrigation pressure using a disposable in-line pressure transducer with integrated pressure sensor (BIOTRANS Disposable Pressure Measuring System, BIOSENSORS International, Newport Beach, Calif.) and digital pressure monitor (EAGLE 3000 patient monitor, MARQUETTE ELECTRONICS, Milwaukee, Wis.). Resistance was calculated from the known flow rate and pressure measurements. We compared pressure generated and resistance between patients with lacrimal drainage obstruction and control patients with no obstruction as determined by clinical exam and dye disappearance testing.

Results

During conventional testing, manual pressure was estimated to deliver 1 cc of saline over an average of 30 seconds for a flow rate of 0.033 milliliters per second. During experimental testing, the syringe pump delivered saline over a flow rate of 0.028 milliliters per second (a known rate of 100 milliliters per hour). Seventeen patients (3 non-obstructive, 14 obstructive) underwent bilateral testing via both conventional probing and irrigation and experimental probing and irrigation via a syringe pump delivery system. The average age was 62.7 years (range, 19 to 95 years).

The average pressure for conventional non-obstructive patients was 101.6 mmHg (range, 46 to 200 mmHg) and calculated resistance was 3078 mmHg×sec/ml. The average pressure for experimental non-obstructive patients was 77.7 mmHg (range, 12 to 209 mmHg) and calculated resistance was 2775 mmHg×sec/ml.

The average pressure for conventional partially obstructed patients was 145.5 mmHg (range, 30 to 300) and calculated resistance was 4409 mmHg×sec/ml. The average pressure for experimental partially obstructed patients was 86.1 mmHg (range, 22 to 266 mmHg) and calculated resistance was 3071 mmHg×sec/ml.

The average pressure for conventional completely obstructed patients was 147.4 mmHg (range, 71 to 242 mmHg) and calculated resistance was 4467 mmHg×sec/ml. The average pressure for experimental completely obstructed patients was 91.9 mmHg (range, 36 to 186 mmHg) and calculated resistance was 3282 mmHg×sec/ml.

From the above description of the invention, those skilled in the art will perceive improvements, changes and modifications. For example, it will be appreciated that detachable member 66 may be an integral part of the syringe body 42 such that the detachable member is not separable from the syringe body. Such improvements, changes, and modifications are within the skill of the art and are intended to be covered by the appended claims.

Having described the invention, the following is claimed:

1. A lacrimal drainage manometer comprising:
a syringe including a syringe body and a piston, said syringe body defining a fluid cavity in fluid communication with a cannula configured for insertion into at least a portion of a lacrimal drainage system, said piston for dispensing a fluid from said fluid cavity through said cannula;
a pressure sensor operably coupled to said syringe and being configured to detect pressure fluid in said fluid cavity;
a fluid flow rate mechanism coupled to said syringe, said fluid flow rate mechanism configured to measure the flow rate of fluid through said syringe; and
a user feedback unit in electrical communication with each of said pressure sensor and said flow sensor, said user feedback unit being operably coupled to said syringe and configured to provide user feedback based on data from said pressure sensor and/or said fluid flow rate mechanism, said user feedback unit comprising a housing having an integrated display for providing said data to a user;
wherein said housing is serially reusable with different syringes and a respective syringe is single-use disposable.

2. The lacrimal drainage manometer of claim 1, wherein said pressure sensor is mounted on a distal surface of said piston.

3. The lacrimal drainage manometer of claim 1, wherein said cannula is integrally formed with a detachable member configured to mate with said syringe body, said detachable member having a lumen extending therethrough, said lumen being in fluid communication with said fluid cavity and said cannula.

4. The lacrimal drainage manometer of claim 1, wherein said housing has an ergonomic, wing-shaped configuration.

5. The lacrimal drainage manometer of claim 4, wherein said syringe body extends through at least a portion of said housing.

6. The lacrimal drainage manometer of claim 1, wherein said housing is configured to releasably engage said syringe body.

7. A method for accurately determining at least one indicator of lacrimal drainage system function during nasolacrimal irrigation, said method comprising the steps of:
    providing a lacrimal drainage manometer comprising a syringe in fluid communication with a cannula, a pressure sensor configured to detect pressure fluid in the fluid cavity and being operably coupled to the syringe, a fluid flow rate mechanism coupled to the syringe and configured to measure the flow rate of fluid through the syringe, and a user feedback unit in electrical communication with each of the pressure sensor and the flow sensor, the user feedback unit comprising a housing having an integrated display for providing data to a user, the housing being serially reusable with different syringes and a respective syringe is single-use disposable;
    inserting a portion of the cannula into a portion of the lacrimal drainage system; and
    quantitatively detecting at least one indicator of lacrimal drainage system function during injection of a fluid through the cannula, the at least one indicator being at least one of nasolacrimal drainage pressure, fluid flow rate or nasolacrimal resistance.

8. The method of claim 7, wherein the portion of the lacrimal drainage system includes an inferior punctum and/or a superior punctum.

9. The method of claim 7, wherein the portion of the lacrimal drainage system includes an inferior canaliculus and/or superior canaliculus.

10. The method of claim 7, wherein said step of quantitatively detecting at least one indicator of lacrimal drainage system function further comprises the step of reading the detected at least one indicator on the user feedback unit.

11. A lacrimal drainage manometer comprising:
    a syringe including a syringe body and a piston, said syringe body defining a fluid cavity in fluid communication with a cannula configured for insertion into at least a portion of a lacrimal drainage system, said piston for dispensing a fluid from said fluid cavity through said cannula;
    a pressure sensor operably coupled to said syringe;
    a fluid flow rate mechanism coupled to said syringe, said fluid flow rate mechanism configured to measure the flow rate of fluid through said syringe; and
    a user feedback unit in electrical communication with each of said pressure sensor and said flow sensor, said user feedback unit being operably coupled to said syringe and configured to provide user feedback based on data from said pressure sensor and/or said fluid flow rate mechanism, said user feedback unit comprising a housing having an integrated display for providing said data to a user, said user feedback unit including a central opening configured to receive a syringe piston;
    wherein said housing is serially reusable with different syringes and a respective syringe is single-use disposable.

* * * * *